(12) United States Patent
Hohlbein

(10) Patent No.: US 9,427,074 B2
(45) Date of Patent: Aug. 30, 2016

(54) ORAL CARE IMPLEMENT

(71) Applicant: COLGATE-PALMOLIVE COMPANY, New York, NY (US)

(72) Inventor: Douglas Hohlbein, Hopewell, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 0 days.

(21) Appl. No.: 14/650,817

(22) PCT Filed: Dec. 10, 2012

(86) PCT No.: PCT/US2012/068670
§ 371 (c)(1),
(2) Date: Jun. 9, 2015

(87) PCT Pub. No.: WO2014/092673
PCT Pub. Date: Jun. 19, 2014

(65) Prior Publication Data
US 2015/0305484 A1    Oct. 29, 2015

(51) Int. Cl.
*A46B 9/04* (2006.01)
*A46B 5/02* (2006.01)
(Continued)

(52) U.S. Cl.
CPC .............. *A46B 5/026* (2013.01); *A46B 5/02* (2013.01); *A46D 3/00* (2013.01); *A61C 17/225* (2013.01); *A46B 5/028* (2013.01); *A46B 2200/1066* (2013.01)

(58) Field of Classification Search
CPC ........ A46B 5/02; A46B 5/026; A46B 5/028; B25G 1/002
USPC ............................................. 15/143.1, 167.1
See application file for complete search history.

(56) References Cited

U.S. PATENT DOCUMENTS

| | | | |
|---|---|---|---|
| 2,094,240 A | 9/1937 | Herrick et al. | |
| 5,325,560 A | 7/1994 | Pavone et al. | |
| 5,630,244 A * | 5/1997 | Chang ................. | A46B 5/0062 15/143.1 |

(Continued)

FOREIGN PATENT DOCUMENTS

| | | |
|---|---|---|
| CN | 101296635 | 10/2008 |
| CN | 102651983 | 8/2012 |

(Continued)

OTHER PUBLICATIONS

International Search Report and the Written Opinion of the International Searching Authority issued in International Patent Application PCT/US2012/068670 mailed Sep. 10, 2013.

(Continued)

*Primary Examiner* — Michael Jennings

(57) ABSTRACT

An oral care implement having a grip component. In one embodiment, the invention can be an oral care implement comprising: an elongated body extending along a longitudinal axis and comprising a head portion and a handle portion; a socket formed in an outer surface of the handle portion, the socket comprising a floor and an open top end; at least one tooth cleaning elements mounted to the head portion of the elongated body; at least one protuberance extending upwardly from the floor of the socket; and a grip component comprising a resilient body formed of a resilient material mounted to the handle portion of the elongated body so as to enclose the open top end of the socket, an inner surface of the resilient body separated from the floor of the socket by a free volume of space.

23 Claims, 10 Drawing Sheets

(51) Int. Cl.
*A61C 17/22* (2006.01)
*A46D 3/00* (2006.01)

(56) References Cited

U.S. PATENT DOCUMENTS

| | | | |
|---|---|---|---|
| 5,713,104 A | 2/1998 | Giampaolo, Jr. | |
| 5,781,958 A * | 7/1998 | Meessmann | A46B 5/02 15/143.1 |
| 5,791,007 A * | 8/1998 | Tsai | A46B 5/0012 15/167.1 |
| 6,066,282 A | 5/2000 | Kramer | |
| 6,273,719 B1 * | 8/2001 | Whitman | A46B 15/0081 15/167.1 |
| 6,464,920 B1 | 10/2002 | Kramer | |
| 6,919,038 B2 | 7/2005 | Meyer et al. | |
| 7,039,984 B1 | 5/2006 | Watanabe et al. | |
| 7,047,591 B2 * | 5/2006 | Hohlbein | A46B 5/02 15/143.1 |
| 7,118,364 B2 | 10/2006 | Morawski | |
| 7,241,413 B2 * | 7/2007 | Pfenniger | A46B 5/00 15/143.1 |
| 7,472,448 B2 | 1/2009 | Hohlbein et al. | |
| 2003/0172483 A1 | 9/2003 | Davis | |
| 2004/0117934 A1 | 6/2004 | Pfenniger et al. | |
| 2005/0066462 A1 | 3/2005 | Moskovich et al. | |
| 2006/0026784 A1 * | 2/2006 | Moskovich | A46B 5/0062 15/110 |
| 2006/0080795 A1 | 4/2006 | Pfenniger et al. | |
| 2006/0213018 A1 * | 9/2006 | Gross | A46B 5/02 15/143.1 |
| 2006/0230652 A1 * | 10/2006 | Little | A46B 5/00 40/314 |
| 2008/0244849 A1 | 10/2008 | Moskovich et al. | |
| 2009/0007359 A1 | 1/2009 | Hohlbein et al. | |
| 2009/0193604 A1 | 8/2009 | Pfenniger et al. | |
| 2011/0067193 A1 * | 3/2011 | Olson | A46B 5/02 15/167.1 |
| 2011/0146015 A1 * | 6/2011 | Moskovich | A46B 5/02 15/167.1 |
| 2011/0167579 A1 | 7/2011 | Huber et al. | |
| 2011/0247158 A1 * | 10/2011 | Jungnickel | G09F 13/06 15/167.1 |
| 2012/0144612 A1 * | 6/2012 | Chen | A46B 9/04 15/143.1 |

FOREIGN PATENT DOCUMENTS

| | | | |
|---|---|---|---|
| CN | 102651984 | 8/2012 | |
| DE | 298 05 323 | 7/1999 | |
| DE | 10 2005 055044 | 5/2007 | |
| EP | 0 580 406 | 1/1994 | |
| FR | 2742318 A1 * | 6/1997 | A46B 5/02 |
| WO | WO9837789 | 9/1998 | |
| WO | WO 00/64306 | 11/2000 | |
| WO | WO 2004/026162 | 4/2004 | |

OTHER PUBLICATIONS

Written Opinion of the International Preliminary Examining Authority issued in International Patent Application PCT/US2012/068670 mailed Feb. 19, 2015.

* cited by examiner

ORAL CARE IMPLEMENT

CROSS-REFERENCE TO RELATED PATENT APPLICATIONS

This application is a U.S. national stage application under 35 U.S.C. §371 of PCT Application No. PCT/US2012/068670, filed Dec. 10, 2012, the entirety of which is incorporated herein by reference.

BACKGROUND OF THE INVENTION

Toothbrushes having grip components that enhance the comfort to a user are known. Specifically, known toothbrushes have been developed whereby a portion of the toothbrush handle that is gripped by a user's thumb is covered with a resilient material in order to provide the user with a comfortable brushing experience. Furthermore, certain grip components have been designed that include projections thereon to further enhance a user's gripping experience and to reduce slippage during use. However, known grip components fail to provide a user with a desired tactile sensation that changes during use of the toothbrush. Thus, a need exists for an improved oral care implement having a grip component.

BRIEF SUMMARY OF THE INVENTION

The present invention is directed to an oral care implement having an improved gripping region. In one aspect, the oral care implement includes a handle and a head. The handle includes a socket formed therein. At least one protuberance extends from a floor of the socket. The socket terminates in an open top end that is closed by a grip component which is coupled to the handle.

In one embodiment, the invention can be an oral care implement comprising: an elongated body extending along a longitudinal axis and comprising a head portion and a handle portion; a socket formed in an outer surface of the handle portion, the socket comprising a floor and an open top end; at least one tooth cleaning element mounted to the head portion of the elongated body; at least one protuberance extending from the floor of the socket; and a grip component comprising a resilient cover mounted to the handle portion of the elongated body to enclose the open top end of the socket such that a space is formed between an inner surface of the resilient cover and the floor of the socket.

In another embodiment, the invention can be an oral care implement comprising: a head having at least one tooth cleaning element; a handle coupled to the head, the handle comprising a socket having a floor and an open top end; a cover coupled to the handle to enclose the open top end of the socket and form a space between an inner surface of the cover and the floor of the socket, the cover formed of a resilient material and the handle formed of a rigid material; and a plurality of protuberances extending from the floor of the socket into the space.

In yet another embodiment, the invention can be a method of manufacturing an oral care implement comprising: a) forming, from a first material, an elongated body comprising a handle portion and a head portion, the handle portion comprising a socket having a floor and an open top end; b) forming at least one protuberance extending upwardly from the floor of the socket; c) forming a cover of a second material; and d) mounting the cover to the handle portion to enclose the open top end of the socket, an inner surface of the cover separated from the floor of the socket by a space.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
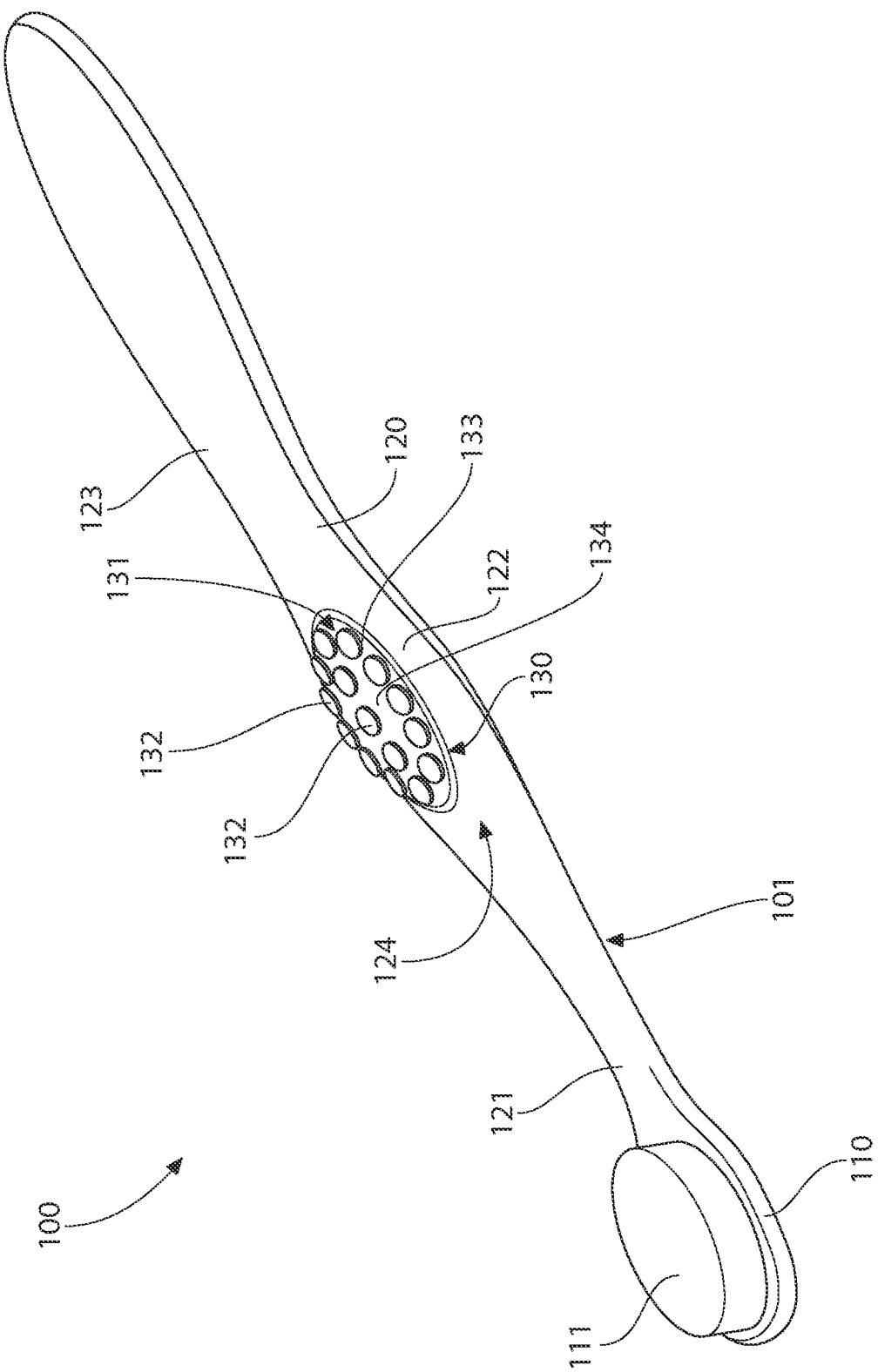
FIG. 1 is a perspective view of an oral care implement in accordance with an embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "top" and "bottom"

as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the exemplified embodiments. Accordingly, the invention expressly should not be limited to such exemplary embodiments illustrating some possible non-limiting combination of features that may exist alone or in other combinations of features; the scope of the invention being defined by the claims appended hereto.

Figure 2:
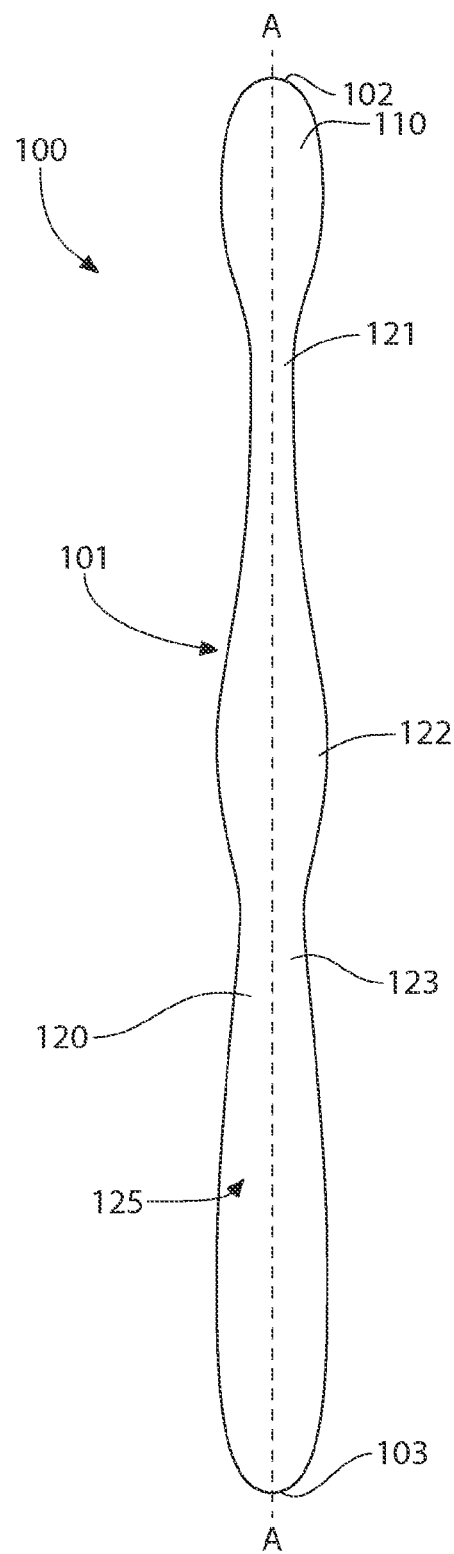
FIG. 2 is a rear view of the oral care implement of FIG. 1.
Figure 3:
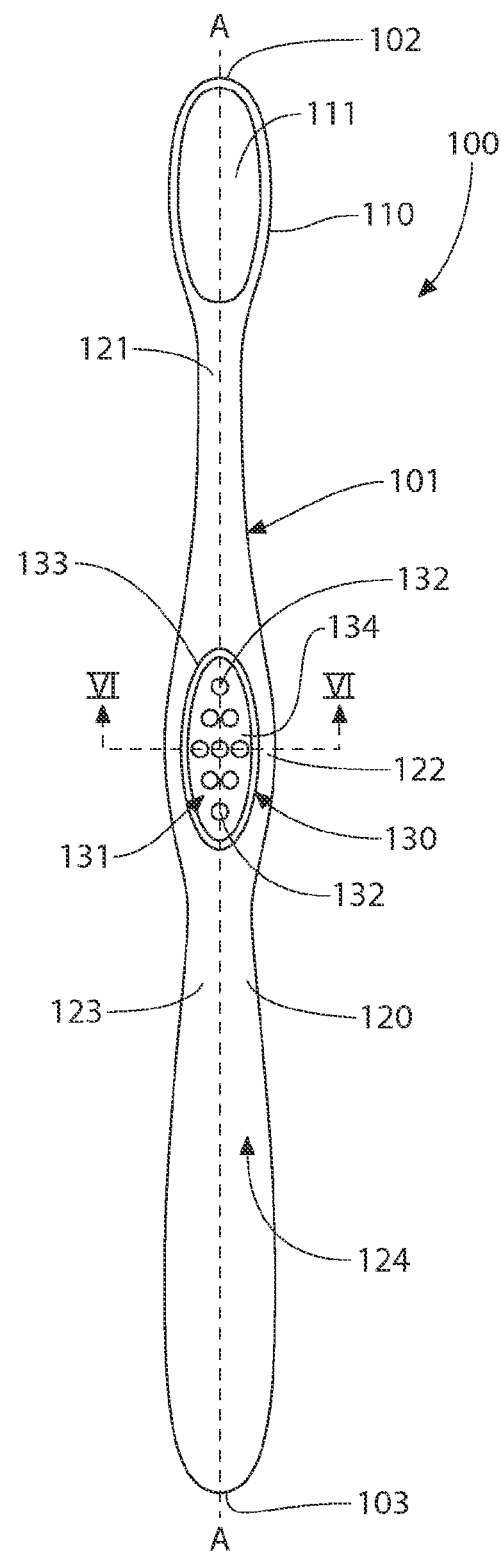
FIG. 3 is a front view of the oral care implement of FIG. 1.

Referring first to FIGS. 1-3 concurrently, an oral care implement 100 in accordance with an embodiment of the present invention will be described. In the exemplified embodiment, the oral care implement 100 is in the form of a manual toothbrush. However, in certain other embodiments the oral care implement 100 can take on other forms such as being a powered toothbrush, a tongue scraper, a gum and soft tissue cleanser, a water pick, an interdental device, a tooth polisher, a specially designed ansate implement having tooth engaging elements or any other type of implement that is commonly used for oral care. Thus, it is to be understood that the inventive concepts discussed herein can be applied to any type of oral care implement unless a specific type of oral care implement is specified in the claims.

The oral care implement 100 generally includes an elongated body 101 comprising a head portion 110 and a handle portion 120. The elongated body 101 of the oral care implement extends from a proximal end 103 to a distal end 102 along a longitudinal axis A-A. The handle portion 120 is an elongated structure that provides the mechanism by which the user can hold and manipulate the oral care implement 100 during use. The handle portion 120 of the oral care implement 100 comprises a neck section 121, a thumb-grip section 122 and a finger grip section 123. The thumb-grip section 122 is located in between the neck section 121 and the finger grip section 123. Furthermore, the handle portion 120 comprises a front surface 124 and an opposing rear surface 125. In certain embodiments, the front surface 124 and the rear surface 125 collectively form an outer surface of the handle portion 120 of the elongated body 101.

In the exemplified embodiment, the handle portion 120 is generically depicted having various contours for user comfort. More specifically, in the exemplified embodiment the thumb-grip section 122 of the handle portion 120 is the widest section of the handle portion 120. Thus, the thumb-grip section 122 has a width that is greater than a width of the neck section 121 of the handle portion 120 and of the finger grip section 123 of the handle portion 120. Of course, the invention is not to be so limited in all embodiments and in certain other embodiments the thumb-grip section 122 may not have a greater width than the neck section 121 and the finger grip section 123. However, the handle portion 120 can take on a wide variety of shapes, contours and configurations, none of which are limiting of the present invention unless so specified in the claims.

In the exemplified embodiment, the handle portion 120 of the elongated body 101 is formed of a rigid plastic material, such as for example without limitation polymers and copolymers of ethylene, propylene, butadiene, vinyl compounds and polyesters such as polyethylene terephthalate. Of course, the invention is not to be so limited in all embodiments and the handle portion 120 may be formed with a resilient material, such as a thermoplastic elastomer, over portions of or the entirety of the handle portion 120 to enhance the gripability of the handle portion 120 during use. For example, portions of the handle portion 120 that are typically gripped by a user's palm during use, such as the finger grip section 123 of the handle portion 120, may be overmolded with a thermoplastic elastomer or other resilient material to further increase comfort to a user.

The head portion 110 of the elongated body 101 is coupled to the handle portion 120. In the exemplified embodiment, the head portion 110 of the oral care implement 100 is provided with a generic block that illustrates tooth cleaning elements 111 extending therefrom. The exact structure, pattern, orientation and material of the tooth cleaning elements 111 is not to be limiting of the present invention unless so specified in the claims. As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The tooth cleaning elements 111 of the present invention can be connected to the head portion 110 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable openings in the tuft blocks so that the base of the bristles is mounted within or below the tuft block.

In certain embodiments, the head portion 110 may also include a soft tissue cleanser coupled to or positioned on its rear surface. An example of a suitable soft tissue cleanser that may be used with the present invention and positioned on the rear surface of the head portion 110 is disclosed in U.S. Pat. No. 7,143,462, issued Dec. 5, 2006 to the assignee of the present application, the entirety of which is hereby incorporated by reference. In certain other embodiments, the soft tissue cleanser may include protuberances, which can take the form of elongated ridges, nubs, or combinations thereof. Of course, the invention is not to be so limited and in certain embodiments the oral care implement 100 may not include any soft tissue cleanser.

In the exemplified embodiment, the head portion 110 is formed integrally with the handle portion 120 as a single unitary structure using a molding, milling, machining or other suitable process. However, in other embodiments the handle portion 120 and the head portion 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners.

A grip component 130 is coupled to the handle portion 120 in the thumb-grip section 122 of the handle portion 120 on the front surface 124 of the handle portion 120. The grip component 130 enhances the comfort to a user during gripping of the oral care implement 100. In the exemplified embodiment the rear surface 125 of the handle portion 120 is a unitary and continuous surface that is devoid of a grip component. Of course, the invention is not to be so limited and in certain embodiments a grip component, such as an overmolded layer of an elastomeric material, may be provided on the rear surface 125 of the handle portion 120. Furthermore, although the invention is illustrated and described herein with the grip component 130 being located on the front surface 124 of the handle portion 120 only, the invention is not to be so limited and the grip component 130 can be located on the rear surface 125 of the handle portion 120 in addition to or instead of being located on the front surface 124 of the handle portion 120. Thus, in certain embodiments there may be a grip component on the rear surface 125 of the handle 120 but not on the front surface 124 of the handle 120. Thus, the grip component 130 may be considered as located on an outer surface of the handle portion 120. In other embodiments, there may be a first grip component (i.e., grip component 130) on the front surface 124 of the handle 120 and a second grip component (not illustrated) on the rear surface 125 of the handle 120. In certain embodiments the front and rear surfaces 124, 125 may merely be first and second surfaces, without any specific correlation between front and rear.

The grip component 130 has a front or outer surface 131 and a plurality of tactile engagement elements 132 protruding from the outer surface 131. The tactile engagement elements 132 enhance the user's gripability on the handle portion 120 of the elongated body 101. The outer surface 131 of the grip component 130 forms a continuous surface with the front surface 124 of the handle portion 120. In the exemplified embodiment, the tactile engagement elements 132 of the grip component 130 are in the shape of columnar projections extending from the outer surface 131 of the grip component 130. However, the invention is not to be so limited in all embodiments and the tactile engagement elements 132 can be in the form of nubs, elongate ridges, or combinations thereof. Furthermore, the exact number, size and shape of the tactile engagement elements 132 are not to be limiting of the present invention in all embodiments unless claimed. In still other embodiments, the tactile engagement elements 132 can be omitted altogether and the outer surfaces 131 of the grip component 130 can be smooth and free of protuberances.

In the embodiment exemplified in FIGS. 1-3, the grip component 130 comprises an annular rim 133 and a resilient cover 134. In certain exemplified embodiments, the resilient cover 134 is a resilient membrane and is formed of a resilient material, such as an injection molded thermoplastic elastomer. However, the invention is not to be so limited and the resilient cover 134 can be formed from other similar materials used in oral care products. As will be appreciated from the description below, in the exemplified embodiment the annular rim 133 provides the mechanism by which the grip component 130 is mounted to the handle portion 120 of the elongated body 101. The annular rim 133 is coupled to the handle portion 120 so as to be flush with the front surface 124 of the handle portion 120. However, in other embodiments the grip component 130 can be mounted to the handle portion 120 by directly coupling the resilient cover 134 to the handle portion 120. In such embodiments (examples of which will be discussed in more detail below) the grip component 130 may include only a resilient cover 134 and the annular rim 133 may be omitted. Furthermore, in the exemplified embodiments the resilient cover 134 is free of penetrations so that when the grip component 130 is coupled to the handle portion 120, an air-tight pocket is formed beneath the resilient cover 134.

Figure 4:
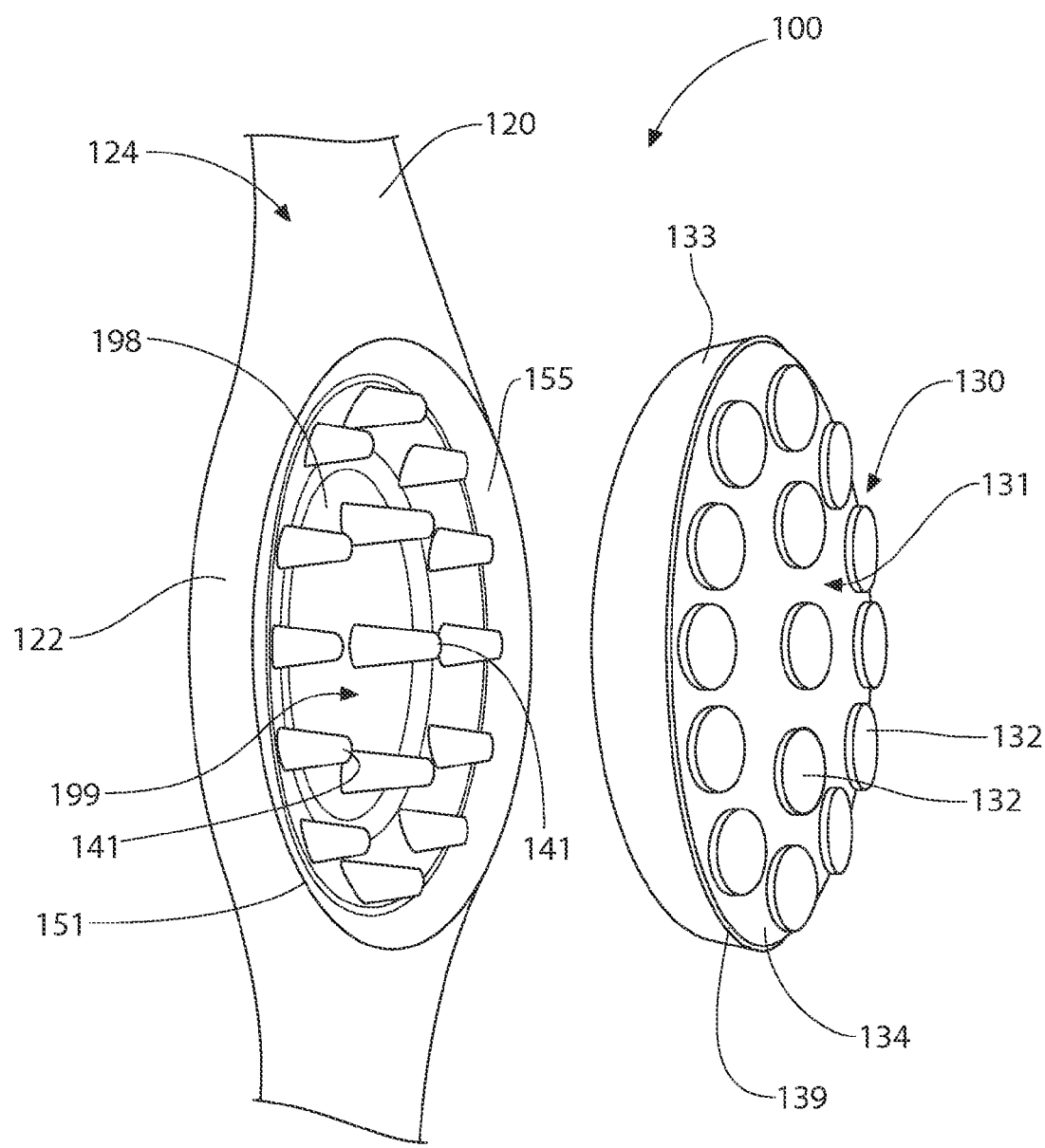
FIG. 4 is a close-up view of a portion of a handle of the oral care implement of FIG. 1 with a grip component separated from the handle.
Figure 5:
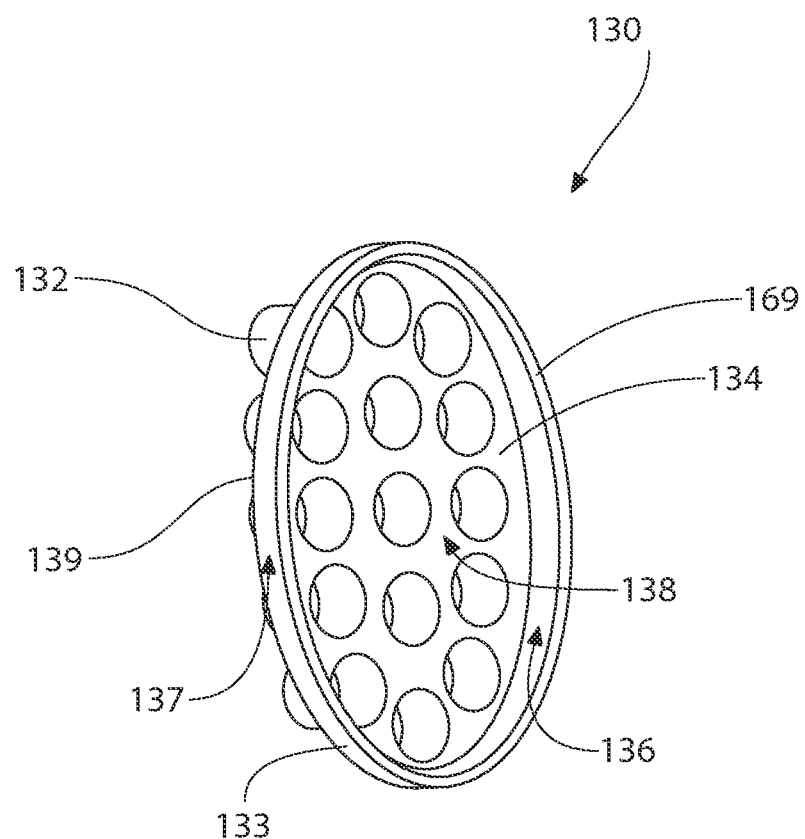
FIG. 5 is a perspective view of the grip component of FIG. 4.

Referring now to FIGS. 4 and 5 concurrently, the oral care implement 100 will be further described. FIGS. 4 and 5 illustrate the grip component 130 having the annular rim 133 and the resilient cover 134. The handle portion 120 comprises a socket 199 formed therein. More specifically, in the exemplified embodiment the socket 199 is formed into the front surface 124 of the handle portion 120. Of course, the invention is not to be so limited and in other embodiments the socket 199 can be formed into the rear surface 125 of the handle portion 120. Thus, for purposes of the invention, the socket 199 can be considered to be formed into the outer surface of the handle portion 120.

In the exemplified embodiment, the socket 199 is an oval shaped basin formed into the thumb-grip section 122 of the handle portion 120 that terminates in an open top end 151 in the front surface 124 of the handle portion 120. The open top end 151 provides a passageway into the socket 199 from the front surface 124 of the handle portion 120. In other embodiments, the socket 199 may be formed into the thumb-grip section 122 of the handle portion 120 and terminate in an open top end that is formed into the rear surface 125 of the handle portion 120. Furthermore, although illustrated as being oval shaped, the invention is not to be so limited and the socket 199 can take on any shape as desired, such as square, rectangular, triangular or any other polygonal shape. The socket 199 is defined by an inner surface 155 of the handle portion 120, the inner surface 155 of the handle portion 120 forming an upstanding perimeter wall that surrounds and defines the socket 199.

In the exemplified embodiment, the socket 199 comprises a floor 198 that forms a lower bounds of the socket 199. As described above, in the exemplified embodiment there is only a single socket 199 located on the front surface 124 of the handle portion 120, and the rear surface 125 of the handle portion 120 is devoid of a socket or opening. However, the invention is not to be so limited in all embodiments and in other embodiments there can be sockets on both the front and rear surfaces 124, 125 of the handle portion 120 with a panel (i.e., a floor) located in between the two sockets.

At least one protuberance 140 extends from the floor 198 of the socket 199. More specifically, the protuberance 140 extends upwardly from the floor 198 of the socket 199 towards the open top end 151. In the exemplified embodiment, a plurality of the protuberances 140 are illustrated extending upwardly from the floor 198 of the socket 199. The invention is not to be limited by the specific number of protuberances 140 or by the pattern of the protuberances 140 in all embodiments. Each of the protuberances 140 has a columnar shape and a circular transverse cross-sectional shape. Furthermore, a height of each of the protuberances 140 extending from the floor 198 of the socket 199 to a free end 141 of the protuberances 140 is greater than a width or diameter of the protuberances 140. However, in other embodiments, depending on the dimensions of the socket 199, the protuberances 140 may have a width or diameter that is greater than its height. As will be discussed in more detail below with reference to FIGS. 6A and 6B, the protuberances 140 provide the user with a tactile sensation during use of the oral care implement 100 by the user compressing the grip component 130 into contact with the protuberances 140.

The annular rim 133 of the grip component 130 comprises an inner surface 136 that defines a central opening 138 and an outer surface 137. The outer surface 137 of the annular rim 133 corresponds in size and shape to the inner surface 155 of the handle portion 120 that defines the socket 199. The resilient cover 134 of the grip component 130 is mounted to the annular rim 133 of the grip component 130 so as to enclose or cover the central opening 138 of the annular ring 133 of the grip component 130. Specifically, the resilient cover 134 is molded to the inner surface 136 of the annular rim 133, the outer surface 137 of the annular rim 133 being free of the first resilient cover 134. Of course, in certain other embodiments the resilient cover 134 may extend onto the outer surface 137 of the annular rim 133.

As described above, the resilient cover 134 covers or encloses the central opening 138 of the annular ring 133 of the grip component 130. The annular ring 133 is merely a ring that is open on both opposing upper and lower ends thereof with a passageway (i.e., the central opening 138) extending therebetween. The resilient cover 134 encloses one of the openings on one of the upper or lower ends of the annular ring 133, thereby completely enclosing that opening. However, the annular ring 133 remains open on its opposite end. By enclosing one of the openings on the upper or lower ends of the annular ring 133, the resilient cover 134 covers the central opening 138. Furthermore, in the exemplified embodiment the resilient cover 134 is free of penetrations to prevent air from passing therethrough.

The resilient cover 134 of the grip component 130 is formed of a resilient material, such as a thermoplastic elastomer. Furthermore, the annular rim 133 of the grip component 130 is formed of a rigid material, such as a hard plastic. In certain embodiment, the material that forms the annular rim 133 of the grip component 130 can be the same as the material that forms the handle portion 120 (and head portion 110) of the elongated body 101 discussed above.

However, it should be appreciated that the annular rim 133 of the grip component 130 may not be rigid despite being formed of a rigid material due to the shape and thickness of the annular rim 133. Specifically, the annular rim 133 is formed of a relatively thin piece of a rigid material, which may cause the annular rim 133 to have some flexibility despite being formed of a rigid material. Furthermore, in the exemplified embodiments the annular rim 133 is oval in shape. However, the invention is not to be limited by the particular shape of the annular rim 133, and the annular rim 133 can take on any other polygonal or closed-geometry shape. Furthermore, in still other embodiments the annular rim 133 need not form a closed-geometry. In the exemplified embodiment, the shape of the annular rim 133 of the grip component 130 matches the shape of the open top end 151 of the socket 199 formed into the handle portion 120.

In the exemplified embodiment, the outer surface 131 of the resilient cover 134 of the grip component 130 is dome-shaped and protrudes from an upper edge 139 of the annular rim 133. Of course, the invention is not to be so limited in all embodiments and in certain other embodiments the outer surface 131 of the resilient cover 134 of the grip component 130 can be flush with the upper edge 139 of the annular rim 133.

Figure 6A:
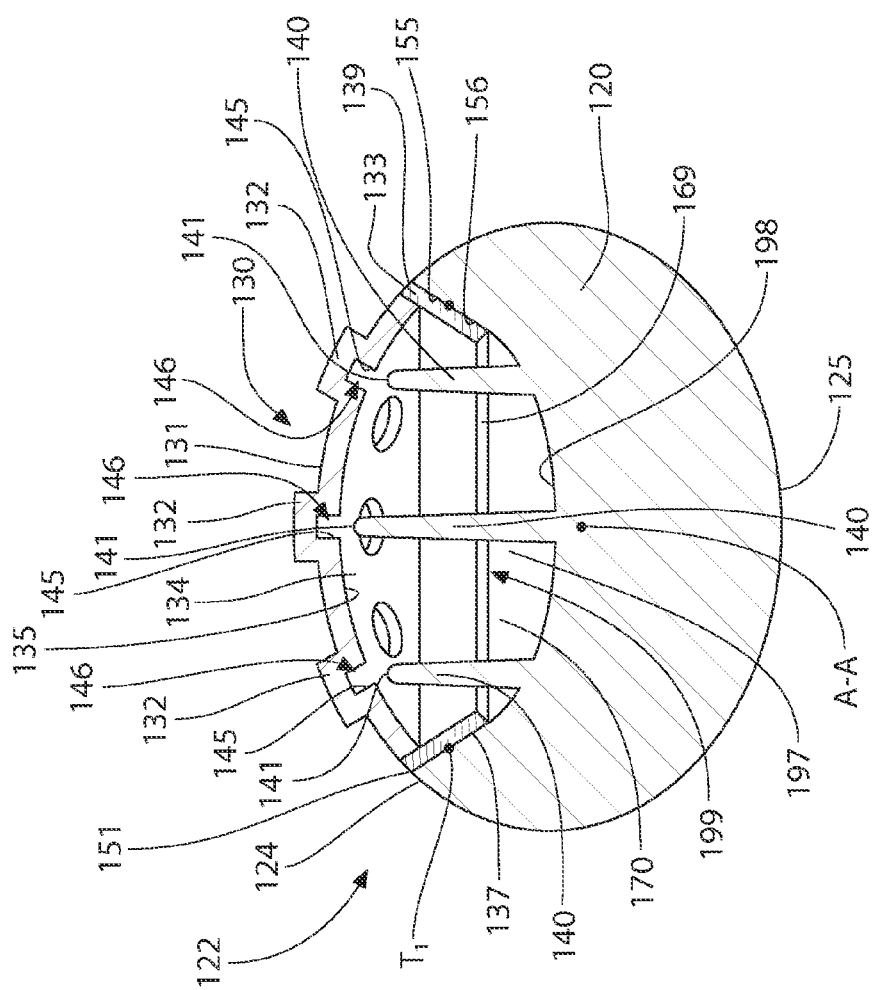
FIG. 6A is a cross-sectional view taken along line VI-VI of FIG. 3, wherein a resilient body of the grip component is in an uncompressed state.
Figure 6B:
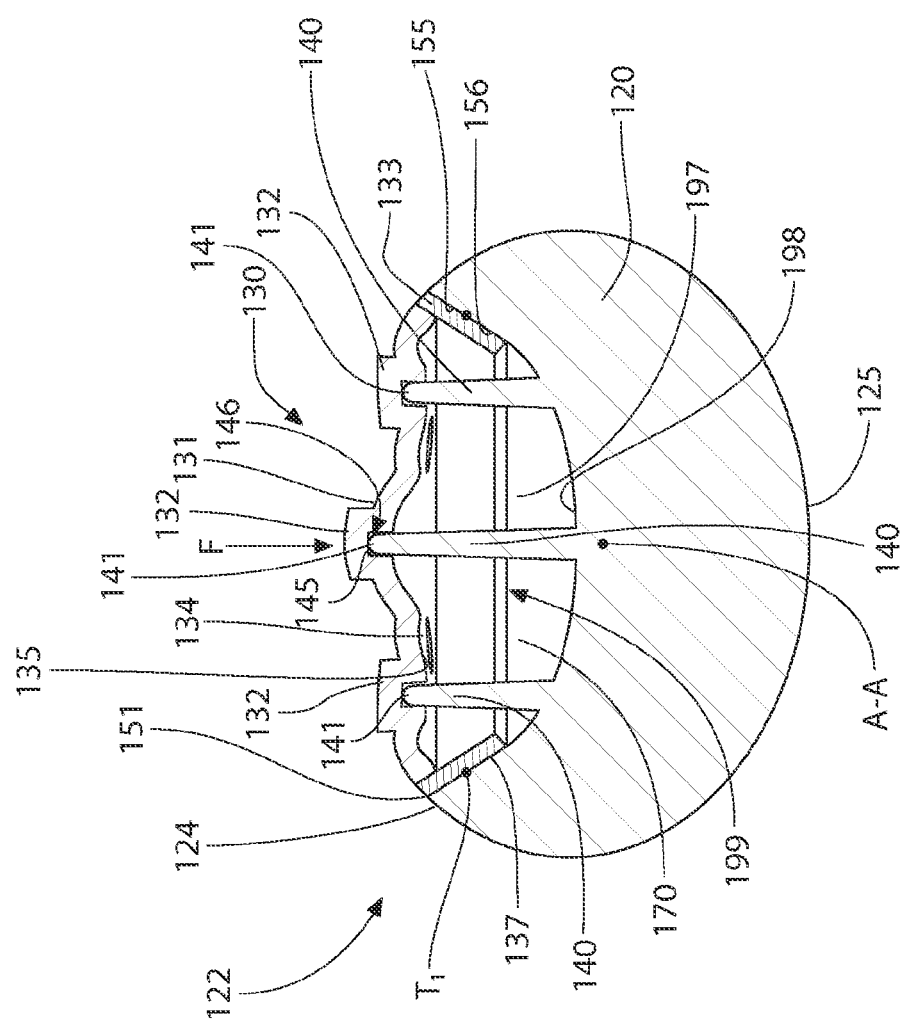
FIG. 6B is the cross-sectional view of FIG. 6A, wherein the resilient body of the grip component is in a compressed state.

Referring to FIGS. 6A and 6B concurrently, the invention will be further described. The cross-sectional view depicted in FIGS. 6A and 6B is taken along line VI-VI of FIG. 3. FIG. 6A illustrates the grip component 130 when there is no force being applied to the outer surface 131 of the resilient cover 134 of the grip component 130 such that the grip component 130 (and more specifically the resilient cover 134 of the grip component 130) is in its natural state. Specifically, in FIG. 6A the resilient cover 134 of the grip component 130 is in its biased uncompressed state. FIG. 6B illustrates the grip component 130 when a force F is being applied to the outer surface 131 of the resilient cover 134 of the grip component 130. Upon the force F being applied to the outer surface 131 of the resilient cover 134 of the grip component 130, the resilient cover 134 of the grip component 130) becomes compressed into a compressed state. When the resilient cover 134 is compressed, the resilient cover 134 contacts one or more of the plurality of protuberances 140. Furthermore, upon release of the force F on the outer surface 131 of the resilient cover 134 of the grip component 130, the resilient cover 134 of the grip component 130 is biased back into the uncompressed state illustrated in FIG. 6A. Thus, the resilient cover 134 is self-biased into the uncompressed state when no force is being applied to the outer surface 131 of the resilient cover 134. In essence, the resilient cover 134 can be considered a spring-like membrane.

The grip component 130 comprises the annular rim 133 and the first resilient cover 134. The outer surface 131 of the first resilient cover 134 is a dome-shaped outer surface that protrudes from the upper edge 139 of the annular rim 133. The upper edge 139 of the annular rim 133 and the dome-shaped outer surface 131 of the first resilient cover 134 form a continuous, uninterrupted and smooth surface with the front surface 124 of the handle portion 120.

As discussed above, the annular rim 133 is formed of a rigid material and the resilient cover 134 is formed of a resilient material. In forming the grip component 130, the resilient cover 134 is molded to the annular rim 133, such as by injection molding. In the exemplified embodiment, the resilient cover 134 is molded to top portions of the annular rim 133 while bottom portions of the annular rim 133 remain free of the resilient cover 134. This is due to the resilient cover 134 being formed as a thin resilient membrane having a thickness that is less than the height of the annular rim 133 (the height of the annular rim 133 extending from bottom edge 169 of the annular rim 133 to the upper edge 139 of the annular rim 133). Of course, the invention is not to be so limited in all embodiments and in certain other embodiments the resilient cover 134 may cover the entire inner surface 136 of the annular rim 133.

In the exemplified embodiment, the outer surface 137 of the annular rim 133 is tapered. Furthermore, the inner surface 155 of the handle portion 120 that defines the socket 199 comprises a tapered sidewall 156. As used herein with regard to the sidewall 156, the term tapered merely indicates that the wall is angled outwardly with distance from the floor 198 of the socket 199 so that the distance between opposing sides of the tapered sidewall 156 increases as the tapered sidewall 156 extends further from the floor 198 of the socket 199 towards the open top end 151. Tapering the sidewalls and the annular rim 133 increases the stability of the grip component 130 within the socket 199 by increasing the attachment between the annular rim 133 of the grip component 130 and the inner surface 155 of the handle portion 120.

In the exemplified embodiment, the tapered outer surface 137 of the annular rim 133 is in abutment with the tapered sidewall 156 of the socket 199. Furthermore, in the exemplified embodiment the outer surface 137 of the annular rim 133 is thermally fused at point $T_1$, such as by ultrasonic welding or otherwise, to the tapered sidewall 156 of the socket 199. An annular interface is formed at the point $T_1$ between the annular rim 133 and the tapered sidewall 156 of the socket 199, thereby forming a hermetic seal along the annular interface so that an air-tight pocket 170 is formed below the resilient cover 134, and more specifically between the resilient cover 134 and the floor 198 of the socket 199. Thus, the grip component 130 is mounted within the socket 199 and encloses the open top end 151 on the front surface 124 of the handle portion 120. It should be appreciated that although the grip component 130 is described as being mounted within the socket 199, this includes instances in which at least a portion of the grip component 130 is disposed within the socket 199 and another portion of the grip component 130 protrudes from the socket 199. In another embodiment, the annular rim 133 includes a full perimeter energy director detail for the purpose of facilitating the ultrasonic welding, to thereby join the annular rim 133 to the body and create an air-tight pocket between the resilient cover 134 and the rigid handle.

As discussed above, in the exemplified embodiment the annular rim 133 of the grip component 130 is thermally fused to the tapered sidewall 156 of the socket 199. However, the invention is not to be so limited in all embodiments and in certain other embodiments mounting the grip component 130 within the socket 199 can be achieved via an interference or tight fit assembly, a coupling sleeve, threaded engagement, adhesion, fasteners or any other known techniques.

Furthermore, in certain embodiments whereby the grip component 130 includes the annular rim 133 and the resilient cover 134, the handle portion 120 may include a shoulder and the annular rim 133 may include a flange such that the interaction between the flange of the annular rim 133 and the shoulder of the handle portion 120 facilitates coupling of the grip component 130 to the handle portion 120. In such an embodiment, after positioning the grip component 130 within the socket 199 as described above, the annular rim 133 is thermally fused to the handle portion 120 using techniques that have been described herein above.

In certain embodiments the grip component 130 may not include an annular rim such that the resilient cover 134 of the grip component can be molded directly to the handle portion 120. Specifically, in certain embodiments the annular rim 133 can be omitted and the resilient cover 134 can be connected directly to the inner surface 155 that defines the socket 199. Such direct connection between the resilient cover 134 and the inner surface 155 can be achieved by injection molding the resilient cover 134 to the inner surface 155. In certain such embodiments the inner surface 155 may comprise a projection extending outwardly therefrom. The projection provides a mechanism for enhancing the attachment between the resilient cover 134 and the handle portion 120. The projection can be an annular protuberance or one or more isolated projections extending from the inner surface 155 of the handle portion 120 inwardly towards the socket 199. Furthermore, in still other embodiments the projection may be altogether omitted and the resilient cover 134 can be injection molded directly onto the flat, smoother inner surface 155 of the handle portion 120. In other embodiments, the projection may be replaced with a recess or slot formed into the inner surface 155 of the handle portion 120 for the resilient material of the resilient cover 134 to flow into when molding the resilient cover 134 to the handle 120. Of course, in other embodiments the inner surface 155 of the handle portion 120 may not include a projection or recess, and the resilient cover 134 of the grip component 130 may be molded to the inner surface 155 of the handle portion 120 using techniques known to persons skilled in the art, including injection molding techniques described herein above.

Thus, utilizing the above features, the grip component 130 can be coupled to the handle portion 120 without the use of the annular rim 133. Due to the lack of an annular rim, the resilient cover 134 of the grip component 130 can be mounted directly to the handle portion 120. In such embodiments, the projection or recess provides a surface for the resilient cover 134 to latch onto to prevent the resilient cover 134 of the grip component 130 from being removed from the socket 199 after being mounted thereto. The resilient cover 134 of the grip component 130 can be mounted to the handle portion 120 by molding the resilient cover 134 directly to the handle portion 120, such as by injection molding.

The resilient cover 134 is compressible into the air-tight pocket 170 in a direction towards the floor 198 of the socket 199 and towards the longitudinal axis A-A of the handle portion 120. The resilient cover 134 is illustrated in the compressed state in FIG. 6B, which occurs as the result of the force F being applied to the outer surface 131 of the resilient cover 134 of the grip component 130. After being compressed inwardly and upon release of the force F on the outer surface 131 of the resilient cover 134 of the grip component 130, the resilient cover 134 biases back into the uncompressed state (illustrated in FIG. 6A).

The resilient cover 134 of the grip component 130 comprises an inner surface 135. Furthermore, as noted above the resilient cover 134 does not completely fill in the empty space within the socket 199. Rather, a space 197 (or air pocket) is formed between the inner surface 135 of the resilient cover 134 of the grip component 130 and the floor 198 of the socket 199. The space 197 is a free volume (such as an air pocket) that is devoid of solid material. The space 197 can be a gas-filled space (such as air-filled space) or can be a liquid-filled space in certain embodiments. Furthermore, in the exemplified embodiment the space 197 forms an air-tight pocket 170. The combination of the grip component 130 and the air-tight pocket 170 creates a more comfortable grip for a user during toothbrushing. Furthermore the grip component 130 uses less material than traditional grip components that completely fill the socket 199, thereby saving costs during manufacturing.

As discussed above, a plurality of protuberances 140 extend upwardly from the floor 198 of the socket 199 in a direction towards the open top end 151. More specifically, in the exemplified embodiment the plurality of protuberances 140 extend upwardly in a direction that is transverse to the longitudinal axis A-A. Each of the protuberances 140 is spaced and isolated from each of the other protuberances 140. Thus, in the exemplified embodiment there is a plurality of isolated, separate and distinct protuberances 140 extending upwardly from the floor 198 of the socket 199. As a result, the space 197 circumferentially surrounds each of the plurality of protuberances 140.

As noted above, each of the protuberances 140 has a columnar shape. Furthermore, in the exemplified embodiment the free ends 141 of the plurality of protuberances 140 are rounded and the protuberances 140 are slightly tapered with distance from the floor 198 of the socket 199 towards the free ends 141. Of course, the invention is not to be so limited in all embodiments and in certain other embodiments the free ends 141 of the protuberances 140 can be pointed, flat, or otherwise shaped. Furthermore, in other embodiments the protuberances 140 may have a constant outer diameter rather than a tapered shape as illustrated. In still other embodiments the protuberances 140 may have a smaller width at the base portions near the floor 198 of the socket 199, and the width of the protuberances 140 may gradually increase from the floor 198 of the socket 199 to the free ends 141 of the protuberances. Such a structural arrangement would make the protuberances 140 more flexible.

In the exemplified embodiment, the free ends 141 of the protuberances 140 are located beyond the open top end 155 of the socket 199. However, the invention is not to be so limited in all embodiments and in certain other embodiments the protuberances 140 may be a height such that the free ends 141 of the protuberances 140 do not extend beyond the open top end 155 of the socket 199. Despite the free ends 141 extending beyond the open top end 155 of the socket, in the exemplified embodiment when the resilient cover 134 is in the uncompressed state (FIG. 6A), the inner surface 135 of the resilient cover 134 is spaced from the protuberances 140, and more specifically from the free ends 141 of the protuberances 140. This is due to the dome-shaped outer surface 131 of the resilient cover 134 of the grip component 130. Thus, the inner surface 135 of the resilient cover 134 is separated from the free ends 141 of the protuberances 140 by a portion of the space 197.

Furthermore, in the exemplified embodiment, upon the force F being applied to the outer surface 131 of the resilient cover 134 of the grip component 130, the resilient cover 134 compresses into the socket 199 and into the compressed state (FIG. 6B). When the resilient cover 134 is compressed into the compressed state, the inner surface 135 of the resilient cover 134 of the grip component 130 contacts the free ends 141 of the protuberances 140. In the exemplified embodiment, the protuberances 140 are arranged such that each of the protuberances 140 is aligned with one of the tactile engagement elements 132 of the resilient cover 134. However, the invention is not to be so limited and the protuberances 140 need not be aligned with the tactile engagement elements 132 in all embodiments.

In the exemplified embodiment, when the resilient cover 134 is compressed into the compressed state, the free ends 141 of the protuberances 140 contact the inner surface 135 of the resilient cover 134 at the tactile engagement elements 132. In the exemplified embodiment, each of the tactile engagement elements 132 has an inner surface 145 that defines a cavity 146 therein. Furthermore, when the resilient cover 134 is compressed into the compressed state, the free ends 141 of the protuberances 140 contact the resilient cover 134 such that the free ends 141 of the protuberances 140 are inserted into the cavities 146 of the tactile engagement elements 132.

Of course, the invention is not to be so limited in all embodiments. In certain embodiments the tactile engagement elements 132 may be omitted and the inner surface 135 of the resilient cover 134 may be a smooth surface. Thus, in such embodiments when the resilient cover 134 is in the compressed state, the free ends 141 of the protuberances 140 merely contact the smooth inner surface of the resilient cover 134. In still other embodiments, the cavities 146 of the tactile engagement elements 132 may be filled with the resilient material such that the free ends 141 of the protuberances 140 can not enter into the cavities 145 when the resilient cover 134 is in the compressed state. In still other embodiments, the protuberances 140 can be offset from the cavities 145 of the tactile engagement elements 132. Regardless of the particular structure of the resilient cover 134 and the protuberances 140 and the relative arrangement therebetween, the free ends 141 of the protuberances 140 come into contact with the inner surface 135 of the resilient cover 134 when the resilient cover 134 is in the compressed state.

Contact between the resilient cover 134 of the grip component 130 and the protuberances 140 provides the user with a unique tactile sensation. Specifically, the user can feel the protuberances 140 through the resilient cover 134 when the resilient cover 134 contacts the protuberances 140. This can be used to provide a warning to a user that he or she is gripping the oral care implement 100 with too much force, or it can be used to provide the user with a massage or other tactile sensation. In certain embodiments, the grip component 130 can be designed so that the force F required to transition the resilient cover 134 into the compressed state is a force that exceeds a predetermined threshold for toothbrushing. Specifically, the invention may be used such that when the user grips the handle portion 120 of the elongated body 101 with too great of a force, the user will be notified of this by the resilient cover 134 achieving the compressed state and contacting the protuberances 140. In other embodiments, the contact between the resilient cover 134 and the protuberances 140 may achieve a massaging effect on a user's thumb such that the user desires to brush with a force F sufficient to achieve the compressed state in order to be rewarded with the massage or tactile sensation. A combination of the thickness of the resilient cover 134 and the height of the protuberances 140 can be used to achieve the desired functionality of the grip component 130.

In the exemplified embodiment of FIGS. 6A and 6B, the free ends 141 of the protuberances 140 collectively form a reference plane having a curvature. Specifically, a reference plane connecting the free ends 141 of the protuberances 140 has an arcuate curvature that has a convex surface facing the resilient cover 134 and a concave surface facing the floor 198 of the socket 199. In the exemplified embodiment, the curvature of the reference plane that connects the free ends 141 of the protuberances 140 corresponds to the curvature of the inner surface 135 of the resilient cover 134. Specifically, the curvature of the reference plane has the same radius of curvature as the curvature of the inner surface 135 of the resilient cover 134. This is achieved by forming a central one of the protuberances 140 to have a height that is greater than the protuberances 140 adjacent thereto so that the protuberance 140 located below the highest part of the dome of the resilient cover 134 has the greatest height. Of course, the invention is not to be limited by the curvature of the reference plane in all embodiments and the relative heights of the protuberances 140 can be other than that illustrated in FIGS. 6A and 6B (see, for example, FIG. 7 which will be discussed in more detail below).

Furthermore, in the exemplified embodiment each of the protuberances 140 is integrally formed with the handle portion 124 of the elongated body 101. Thus, in the exemplified embodiment the protuberances 140 are formed of a rigid plastic material, such as for example without limitation polymers and copolymers of ethylene, propylene, butadiene, vinyl compounds and polyesters such as polyethylene terephthalate. The invention is not to be so limited in all embodiments and in certain other embodiments the protuberances 140 can be formed of a material that is different than the material of the handle portion 120. For example, the protuberances 140 can be formed of a resilient material, such as a thermoplastic elastomer. In such embodiments, the resilient material may be the same as the material of the resilient cover 134, or the resilient material may have a greater hardness than the hardness of the material of the resilient cover 134 to prevent the protuberances 140 from collapsing upon contact by with the resilient cover 134. In still other embodiments, the protuberances 140 may be formed with a core formed from a rigid material and a shell formed from a resilient material to provide a combination of durability and comfort. In further embodiments, some of the protuberances 140 can be integrally formed with the elongated body 101 out of the rigid material and others of the protuberances 140 can be separately formed from the elongated body 101 out of a resilient material.

In certain embodiments, the resilient cover 134 is formed of a transparent or translucent material. In such embodiments, the protuberances 140 are visible through the resilient cover 134. In this manner, a user viewing the oral care implement 100 can see the protuberances 140 through the resilient cover 134 prior to and during use of the oral care implement 100. This will provide the oral care implement 100 with an enhanced aesthetic and serve as an informative feature by enabling a consumer or potential purchaser to see the massaging or pressure warning feature prior to purchase thereof.

Figure 7A:
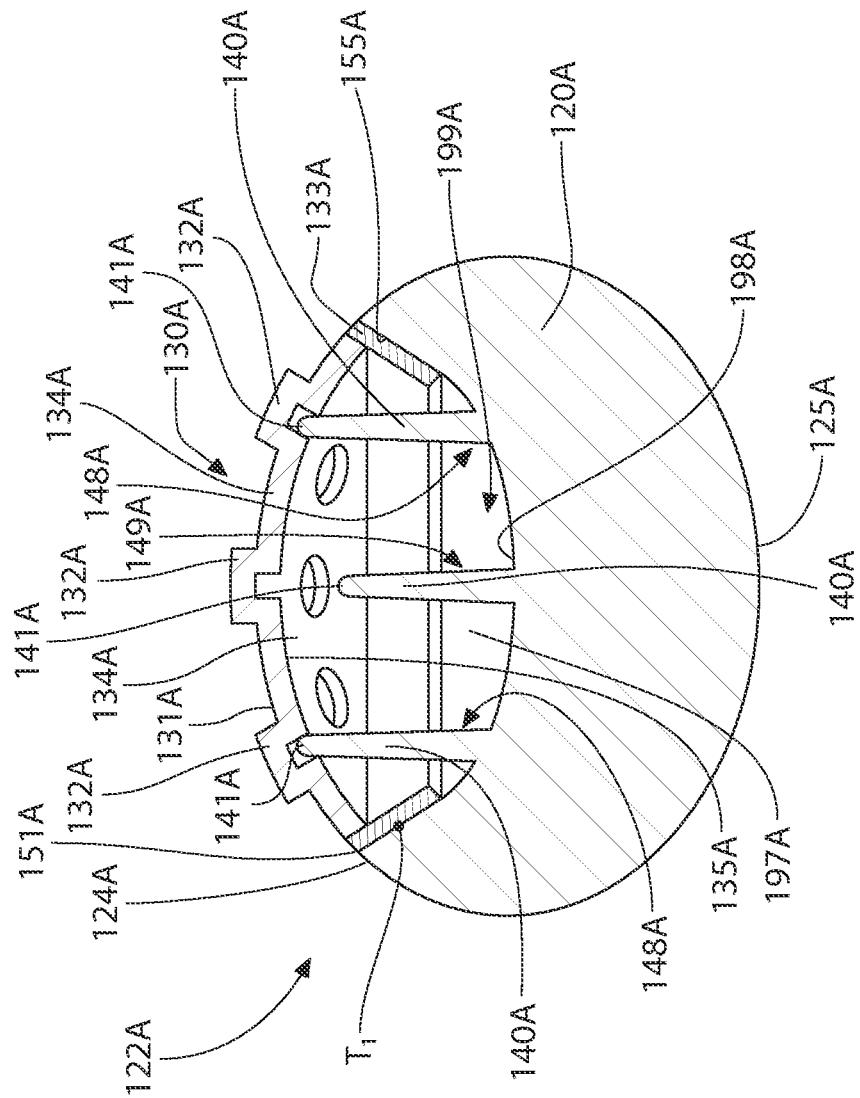
FIG. 7A is an alternative embodiment of the cross-sectional view of FIG. 6, wherein the resilient body of the grip component is in the uncompressed state.
Figure 7B:
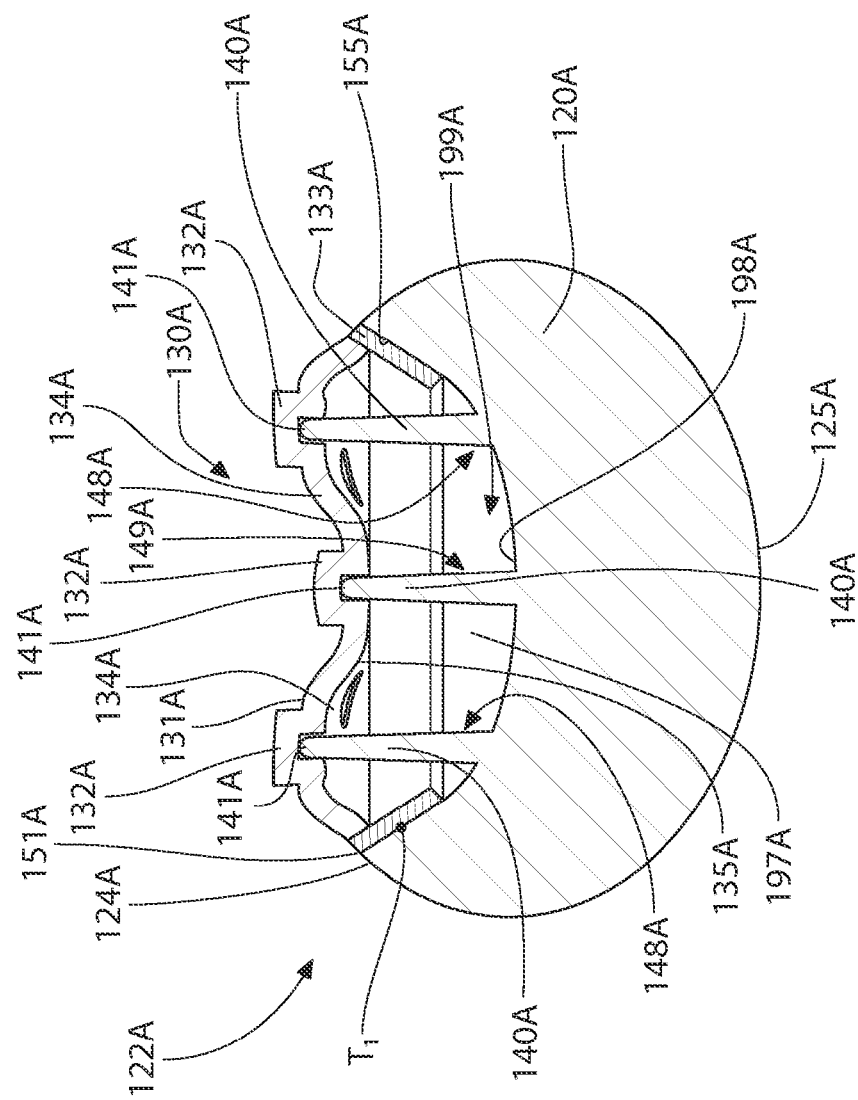
FIG. 7B is the cross-sectional view of FIG. 7A, wherein the resilient body of the grip component is in the compressed state.
Figure 8:
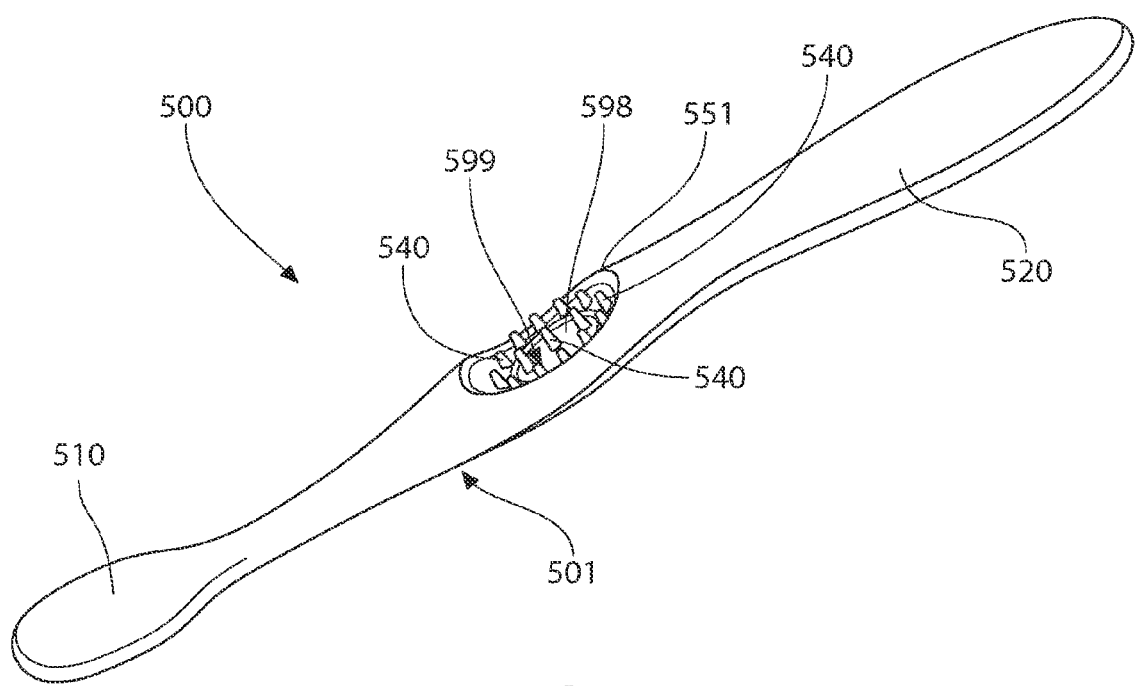
FIG. 8 is a perspective view of an elongated body of an oral care implement in accordance with an embodiment of the present invention.
Figure 9:
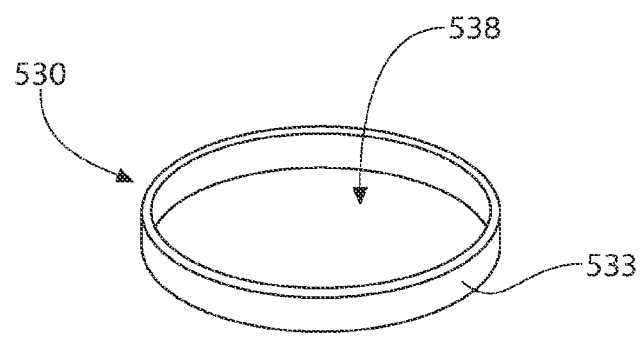
FIG. 9 is a perspective view of an annular rim of a grip component in accordance with an embodiment of the present invention.

Turning now to FIGS. 7A and 7B concurrently, an alternative embodiment of a thumb-grip section 122A of the oral care implement 100 will be described. The thumb-grip section 122A is similar to the thumb-grip section 122 described above and depicted in FIGS. 6A and 6B. Thus, only the structural components of the thumb-grip section 122A that are different than the thumb-grip section 122 will be discussed herein below with the understanding that the description above with regard to FIGS. 1-6B applies to all other structural components. Furthermore, the components of the thumb-grip section 122A will have the same reference numerals as similar components from the thumb-grip section 122 except that the suffix "A" will be used. It will be understood that features that are not described below are the same as its similarly numbered feature described above. Specifically, the grip component 130A is substantially similar to the grip component 130 described above. Thus, a detailed description of the grip component 130A will be not provided below, with the understanding that the description above applies.

In the embodiment exemplified in FIGS. 7A and 7B, a plurality of protuberances 140A protrude upwardly from the floor 198A of the socket 199A. Furthermore, FIG. 7A illustrates the resilient cover 134A of the grip component 130A in a biased uncompressed state, and FIG. 7B illustrates the resilient cover 134A of the grip component 130A in a compressed state (which is achieved by application of the force F onto the outer surface 131A of the resilient cover 134A). The difference between the embodiment exemplified in FIGS. 7A and 7B and the embodiment exemplified in FIGS. 6A and 6B is the relative height of the protuberances 140A. Specifically, in FIGS. 7A and 7B, the protuberances 140A include a first set of protuberances 148A and a second set of protuberances 149A. In the exemplified embodiment, the protuberances 140A of the second set of protuberances 149A are positioned in between the protuberances 140A of the first set of protuberances 148A.

In FIG. 7A, wherein the resilient cover 134A is in the biased and uncompressed state (i.e., no force is being applied to the outer surface 131A of the resilient cover 134A), the free ends 141A of the protuberances 140A of the first set of protuberances 148A are in contact with the inner surface 135A of the resilient cover 134A and the free ends 141A of the protuberances 140A of the second set of protuberances 149A are spaced from the inner surface 135A of the resilient cover 134A. Thus, in the embodiment exemplified in FIG. 7A, a user will feel the sensation of the protuberances 140A of the first set of protuberances 148A even without compressing the resilient cover 134A into the compressed state. However, as illustrated in FIG. 7B, a force F applied to the outer surface 131A of the resilient cover 134A will compress the portions of the resilient cover 134A that are spaced from the protuberances 140A (such as the portions aligned with and above the protuberances 140A of the second set of protuberances 149A) until the inner surface 131A of the resilient cover 134A contacts those protuberances 140A. Thus, the protuberances 140A can be used to limit or otherwise control the areas of compressibility of the resilient cover 134A, which will affect the resulting tactile sensation felt by a user during toothbrushing.

Of course, the invention is not to be particularly limited by the relative heights of the protuberances 140, 140A as illustrated in the figures provided herewith. The protuberances 140, 140A can take on many different configurations to achieve many different tactile experiences and pressure sensor warnings as desired. Thus, the invention is not to be particularly limited by the configuration, pattern, arrangement, size, shape and/or number of the protuberances 140, 140A unless so specified in the claims.

Referring now to FIGS. 8-11 concurrently, a method of manufacturing an oral care implement 500 having the features discussed herein will be described. In manufacturing the oral care implement 500, first an elongated body 501 comprising a handle portion 520 and a head portion 510 is formed from a first material, the first material being a hard plastic. The elongated body 501 is formed so as to have a socket 599 formed into the handle portion 520. The socket 599 has a floor 598 and an open top end 551. Forming the elongated body 501 includes forming a first mold cavity and injecting a molten form of the first material into the first mold cavity, the first mold cavity having a shape that corresponds to the shape of the elongated body 501. After injecting the molten form of the first material into the first mold cavity, the molten form of the first material is allowed to cool within the first mold cavity, thereby forming the elongated body 501 having the socket 599 formed therein.

Next, at least one protuberance 540 is formed so as to extend upwardly from the floor 598 of the socket 599. In certain embodiments, the protuberances 540 can be formed integrally with the elongated body 501 such that the first mold cavity includes shaping that corresponds to the shape of the protuberances 540. In such embodiments, the formation of the elongated body 501 and the protuberances 540 are achieved concurrently in a single injection molding step. In other embodiments, the protuberances 540 can be separately formed from and later connected to the floor 598 of the socket 599 by any means known in the art. For example, the protuberances 540 can be formed from a resilient material, such as an injection molded thermoplastic. In other embodiments the protuberances 540 can be formed of a rigid material that is similar to the material of the elongated body 501, but the protuberances 540 can simply be formed separately from the elongated body 501 and later connected thereto.

Next, a grip component 530 is formed. In certain embodiments, the grip component 530 may include only a cover 534 formed of a second material. However, in other embodiments the grip component 530 comprises an annular rim 533 having a central opening 538 and the cover 534. The annular rim 533 is formed of a third material. In certain embodiments, the first material that forms the elongated body 501 is the same as the third material that forms the annular rim 533. However, the invention is not to be so limited in all embodiments. Nonetheless, it is preferable that both the first and third materials are rigid materials, such as has been described herein above.

Figure 10:
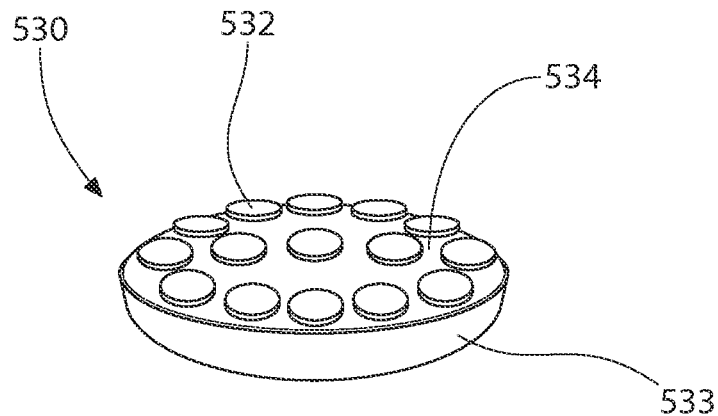
FIG. 10 is a perspective view of a grip component in accordance with an embodiment of the present invention.
Figure 11:
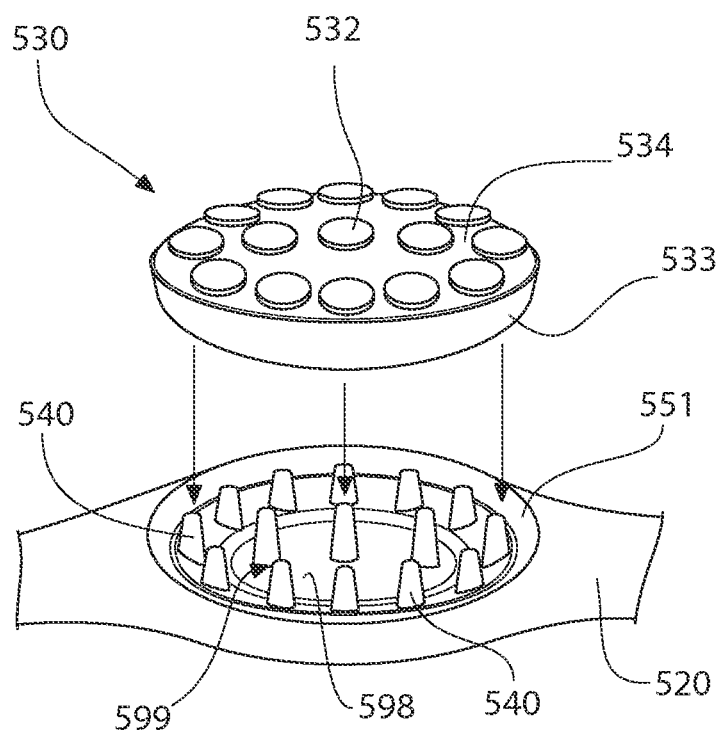
FIG. 11 is a perspective view illustrating mounting the grip component of FIG. 10 into a socket of a handle of an oral care implement.

Forming the annular rim 533 includes forming a second mold cavity and injecting a molten form of the third material into the second mold cavity, the second mold cavity having a shape that corresponds to the shape of the annular rim 533. Next, the molten form of the third material within the second mold is allowed to cool, thereby forming the annular rim 533. After forming the annular rim 533, the cover 534 is mounted to the annular rim 533 so as to cover the opening 538 in the annular ring 533. The cover 534 is formed of a second material. In certain embodiments, the second material is more resilient than the first and third materials, and more specifically the second material can be a thermoplastic elastomer. To form the cover 534 and mold the cover 534 onto the annular ring 533, a third mold cavity is formed at the central opening 538 of the annular rim 533 and a molten form of the second material is injected into the third mold cavity into contact with the annular rim 533. The third mold cavity has a shape that corresponds to the first cover 534, including any tactile engagement elements 532 that are extending from the first cover 534. Finally, the molten form of the second material is allowed to cool within the third mold cavity, thereby forming the grip component 530 in which the cover 534 is molded to the annular rim 533. In the exemplified embodiments, the first and third materials are rigid materials and the third material is a resilient material. FIG. 10 illustrates the first grip component 530 having the cover 534 molded onto the annular rim 533.

Although the invention has been described herein with the grip component 530 including the annular rim 533 and the cover 534, the invention is not to be so limited in all embodiments. In certain embodiments, the grip component 530 may include only a cover 534 formed of the second material. In such embodiments, the annular rim 533 is omitted.

After forming the elongated body 501 and the first grip component 530, the first grip component 530 is mounted within the socket 599 of the handle portion 520 of the elongated body 501. This includes positioning the grip component 530 within the socket 599 of the handle portion 520 and thermally fusing the annular rim 533 of the grip component 530 to the handle portion 520, thereby securing the grip component 530 to the handle portion 520. Of course, as has been discussed above the grip component 530 may otherwise be secured to the handle portion 520, such as be utilizing an interference fit, adhesion, fasteners or the like. Further still, in embodiments that omit the annular rim 533, the cover 534 may be injection molded directly into the socket 599 to enclose the open top end 551 of the socket 599. Upon mounting the cover 534 to the handle portion 520 to enclose the open top end 551 of the socket 599, an inner surface of the cover 534 is separated from the floor 598 of the socket 599 by a space.

Upon securing the annular rim 533 to the handle portion 520 (or otherwise securing the grip component 530 to the handle portion 520), the grip component 530 covers and encloses the open top end 551 of the socket 599. As a result, an air-tight pocket is formed beneath the cover 534 of the grip component 530. This provides a comfortable gripping component for a user during use of the oral care implement 500.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care implement comprising:
    an elongated body extending along a longitudinal axis and comprising a head portion and a handle portion;
    a socket formed in an outer surface of the handle portion, the socket comprising a floor and an open top end;
    at least one tooth cleaning element mounted to the head portion of the elongated body;
    a plurality of protuberances extending upwardly from the floor of the socket towards the open top end of the socket, wherein the protuberances are integrally formed with the elongated body; and
    a grip component comprising a resilient cover mounted to the handle portion of the elongated body to enclose the open top end of the socket such that a space is formed between an inner surface of the resilient cover and the floor of the socket.

2. The oral care implement of claim 1 wherein the grip component further comprises an annular rim defining a central opening, the annular rim formed of a rigid material and the resilient cover formed of a resilient material, the resilient cover mounted to the annular rim to enclose the central opening.

3. The oral care implement according to claim 2 wherein the handle portion is formed of a rigid material, the annular rim thermally fused to the handle portion.

4. The oral care implement according to claim 2 wherein an annular interface is formed between the annular rim and the handle portion, and wherein a hermetic seal is formed along the annular interface so that the space is an air-tight pocket.

5. The oral care implement according to claim 1 wherein the resilient cover has a dome-shaped outer surface and a plurality of tactile engagement elements protruding from the dome-shaped outer surface, each of the protuberances aligned with one of the tactile engagement elements of the resilient cover.

6. The oral care implement according to claim 1 wherein the resilient cover of the grip component is compressible from an uncompressed state to a compressed state upon application of a force to an outer surface of the resilient cover, and wherein the inner surface of the resilient cover is spaced-apart from free ends of the protuberances when the resilient cover is in the uncompressed state, the resilient cover being self-biased into the uncompressed state.

7. The oral care implement according to claim 6 wherein the resilient cover of the grip component is compressible in a direction towards the longitudinal axis of the elongated body when the force is applied to the outer surface of the resilient cover, and wherein when the resilient cover is in the compressed state the resilient cover contacts the free ends of the protuberances.

8. The oral care implement according to claim 1 wherein the plurality of protuberances are spaced and isolated from one another.

9. The oral care implement according to claim 1 wherein each of the plurality of protuberances extend upwardly from the floor of the socket towards the open top end of the socket, the space being a free volume that circumferentially surrounds each of the plurality of protuberances.

10. The oral care implement according to claim 1 wherein free ends of the plurality of protuberances collectively form a reference plane having a curvature that corresponds to a curvature of the inner surface of the resilient cover.

11. The oral care implement according to claim 1 wherein the elongated body and the protuberances are formed of a rigid plastic.

12. The oral care implement according to claim 1 wherein the resilient cover is formed of a transparent or translucent material.

13. The oral care implement according to claim 1 wherein each of the protuberances has a columnar shape, and wherein each of the protuberances has a height, measured from the floor of the socket to a free end of the protuberance, that is greater than a width of the protuberance.

14. The oral care implement according to claim 1 wherein the protuberances have a rounded free end.

15. The oral care implement according to claim 1 wherein the protuberances extend from the floor in a direction that is transverse to the longitudinal axis of the elongated body.

16. The oral care implement according to claim 1 further comprising a first set of protuberances extending upwardly from the floor of the socket and a second set of protuberances extending upwardly from the floor of the socket, wherein when the resilient cover is in an uncompressed state, an inner surface of the resilient cover is in contact with the first set of protuberances and spaced from the second set of protuberances.

17. The oral care implement according to claim 1 wherein the resilient cover is transparent or translucent so that the protuberance is visible through the resilient cover.

18. An oral care implement comprising:
a head having at least one tooth cleaning element;
a handle coupled to the head, the handle comprising a socket having a floor and an open top end;
a cover coupled to the handle to enclose the open top end of the socket and form a space between an inner surface of the cover and the floor of the socket, the cover formed of a resilient material and the handle formed of a rigid material; and
a plurality of protuberances extending from the floor of the socket into the space, wherein the protuberances are integrally formed with the handle.

19. The oral care implement according to claim 18 wherein the plurality of protuberances are formed out of the rigid material, and wherein the resilient material is a thermoplastic elastomer and the rigid material is a hard plastic.

20. The oral care implement according to claim 18 wherein the plurality of protuberances are isolated from one another, and wherein the space is a free-volume that circumferentially surrounds each of the plurality of protuberances.

21. The oral care implement according to claim 18 wherein upon application of a force onto an outer surface of the resilient body, the resilient body is compressed into contact with one or more of the plurality of protuberances.

22. The oral care implement according to claim 18 wherein the space is hermetically sealed.

23. A method of manufacturing an oral care implement comprising:
a) forming, from a first material, an elongated body comprising a handle portion and a head portion, the handle portion comprising a socket having a floor and an open top end;
b) forming at least one protuberance extending upwardly from the floor of the socket;
c) forming a cover of a second material; and
d) mounting the cover to the handle portion to enclose the open top end of the socket, an inner surface of the cover separated from the floor of the socket by a space; and
wherein steps a) and b) are performed concurrently in a single injection molding step.

* * * * *